US011083609B2

United States Patent
Malsbary et al.

(10) Patent No.: US 11,083,609 B2
(45) Date of Patent: Aug. 10, 2021

(54) SELECTABLE TIP DELIVERY SYSTEM AND METHOD

(71) Applicant: Medtronic Vascular, Inc., Santa Rosa, CA (US)

(72) Inventors: Todd Malsbary, Windsor, CA (US); Mark Rowe, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 137 days.

(21) Appl. No.: 15/960,613

(22) Filed: Apr. 24, 2018

(65) Prior Publication Data
US 2019/0321592 A1    Oct. 24, 2019

(51) Int. Cl.
| A61M 25/00 | (2006.01) |
| A61F 2/95 | (2013.01) |
| A61F 2/966 | (2013.01) |
| A61M 39/12 | (2006.01) |

(52) U.S. Cl.
CPC ............. *A61F 2/966* (2013.01); *A61F 2/95* (2013.01); *A61M 25/002* (2013.01); *A61M 25/0069* (2013.01); *A61M 39/12* (2013.01); *A61F 2250/0062* (2013.01); *A61M 2209/06* (2013.01)

(58) Field of Classification Search
CPC ............ A61M 5/0262; A61M 25/00; A61M 25/0069; A61M 25/002; A61M 39/12; A61B 2/05; A61F 2/2427; A61F 2/2436; A61F 2/95; A61F 2/962; A61F 2/966; A61F 2/011; A61F 2/013

See application file for complete search history.

(56) References Cited

U.S. PATENT DOCUMENTS

| 4,779,727 A | * | 10/1988 | Taterka | A61M 25/002 206/364 |
| 5,058,580 A | * | 10/1991 | Hazard | A61M 16/0465 128/207.15 |
| 5,569,197 A | * | 10/1996 | Helmus | A61M 25/09 604/102.02 |

(Continued)

FOREIGN PATENT DOCUMENTS

| EP | 1290986 A2 | 3/2003 | |
| GB | 2103936 A | * 3/1983 | ........ A61M 25/0069 |
| WO | 2012023981 A2 | 2/2012 | |

OTHER PUBLICATIONS

PCT/US2019/024285, The International Search Report and the Written Opinion, dated Jun. 19, 2019, 12pgs.

*Primary Examiner* — Diane D Yabut
*Assistant Examiner* — Christian D Knauss
(74) *Attorney, Agent, or Firm* — Innovation Counsel LLP

(57) ABSTRACT

A delivery system for delivering a prosthesis includes a catheter and a selectable tip kit having a plurality of tips. Each tip is uniquely shaped, i.e., has a particular shape different than the shape of all the other tips, and each tip is better suited for some procedures than for others. One of the tips is selected by the physician as being particularly well suited for the procedure to be performed. The selected tip is non-removably attached to the catheter and the remaining tips are discarded. This allows the delivery system to be customizable to each procedure, putting the physician in control of the case. This provides a case specific delivery system for the physicians to use and at a very low expense and with minimal additional engineering.

18 Claims, 12 Drawing Sheets

(56) References Cited

U.S. PATENT DOCUMENTS

| | | | | |
|---|---|---|---|---|
| 6,322,586 | B1* | 11/2001 | Monroe | A61F 2/95 606/108 |
| 6,918,920 | B1* | 7/2005 | Wang | A61M 25/0069 606/194 |
| 7,172,619 | B2* | 2/2007 | Richter | A61F 2/958 623/1.11 |
| 9,044,286 | B2* | 6/2015 | O'Neil | B25B 23/1427 |
| 9,119,603 | B2* | 9/2015 | Bright | A61B 17/00234 |
| 9,314,360 | B2* | 4/2016 | Kao | A61F 2/95 |
| 2004/0093063 | A1* | 5/2004 | Wright | A61F 2/95 623/1.12 |
| 2008/0228255 | A1* | 9/2008 | Rust | A61F 2/95 623/1.11 |
| 2008/0262590 | A1* | 10/2008 | Murray | A61F 2/95 623/1.11 |
| 2009/0264858 | A1* | 10/2009 | Nash | A61M 25/0069 604/508 |
| 2010/0004732 | A1* | 1/2010 | Johnson | A61F 2/95 623/1.11 |
| 2010/0268317 | A1* | 10/2010 | Stiger | A61F 2/95 623/1.12 |
| 2013/0274860 | A1* | 10/2013 | Argentine | A61F 2/9517 623/1.12 |
| 2015/0073391 | A1* | 3/2015 | Hutchins | A61M 25/0147 604/528 |
| 2017/0325934 | A1* | 11/2017 | Gilani | A61F 2/07 |

* cited by examiner

SELECTABLE TIP DELIVERY SYSTEM AND METHOD

BACKGROUND

Field

The present application relates to an intra-vascular device and method. More particularly, the present application relates to a device for treatment of intra-vascular diseases.

Description of the Related Art

A conventional stent-graft (endovascular prosthesis) typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

The stent-graft is delivered within a delivery system to the deployment location. Depending upon the particular application and deployment location, a particular delivery system must be used. This necessitates that several different delivery systems be available for the physician.

SUMMARY

A delivery system for delivering a prosthesis includes a catheter and a selectable tip kit having a plurality of tips. Each tip is uniquely shaped, i.e., has a particular shape different than the shape of all the other tips, and each tip is better suited for some procedures than for others. One of the tips is selected by the physician as being particularly well suited for the procedure to be performed. The selected tip is non-removably attached to the catheter and the remaining tips are discarded. This allows the delivery system to be customizable to each procedure, putting the physician in control of the case. This provides a case specific delivery system for the physicians to use and at a very low expense and with minimal additional engineering.

Embodiments are best understood by reference to the following detailed description when read in conjunction with the accompanying drawings.

BRIEF DESCRIPTION OF DRAWINGS

Common reference numerals are used throughout the drawings and detailed description to indicate like elements.

DETAILED DESCRIPTION

Figure 1:
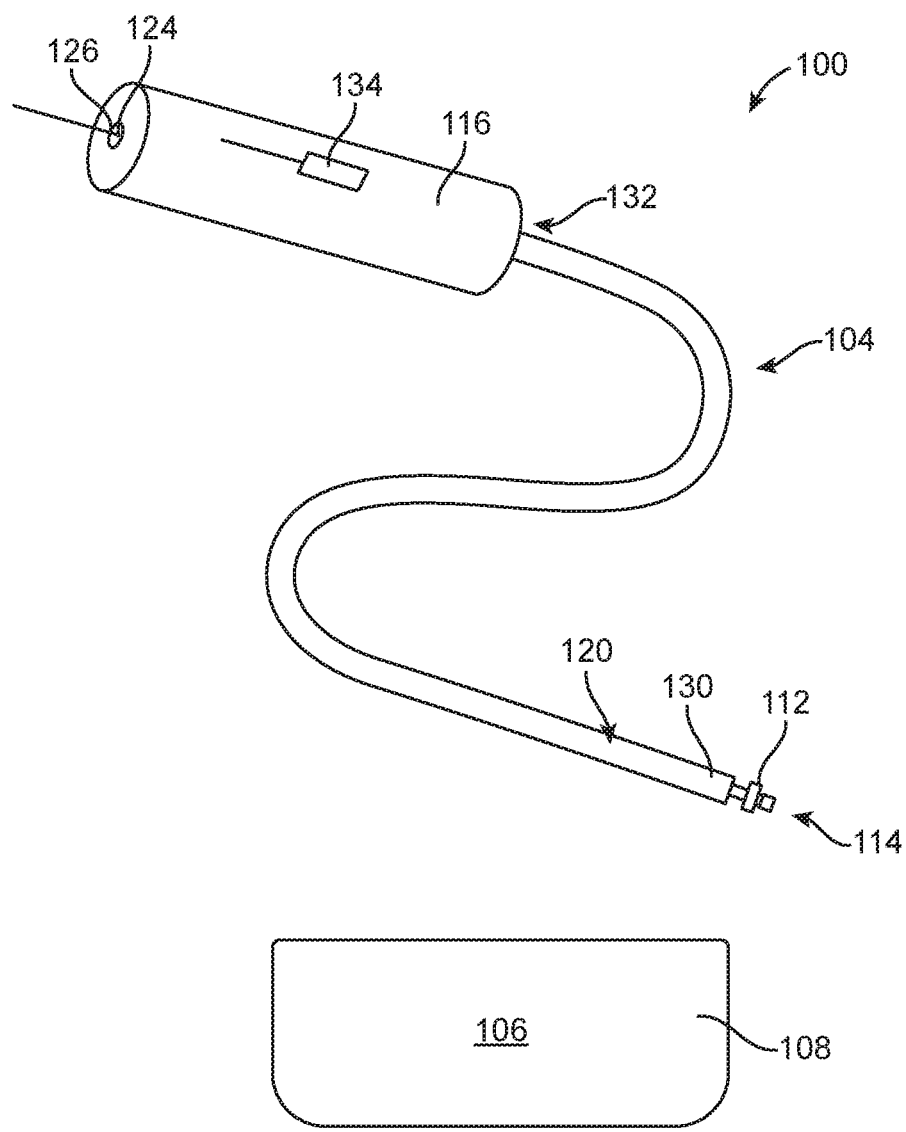
FIG. 1 is a perspective view of a delivery system for deploying a prosthesis in a pre-tip attachment state in accordance with one embodiment.

FIG. 1 is a perspective view of a delivery system 100 for deploying a prosthesis 102 (see FIG. 3) in a pre-tip attachment state in accordance with one embodiment. Delivery system 100, sometimes called a vascular stent-graft delivery system, includes a catheter 104 and selectable tip kit 106. In FIG. 1, selectable tip kit 106 is closed and illustrates a container 108 containing tips. For example, FIG. 1 is representative of how delivery system 100 is provided to a physician.

Figure 2:
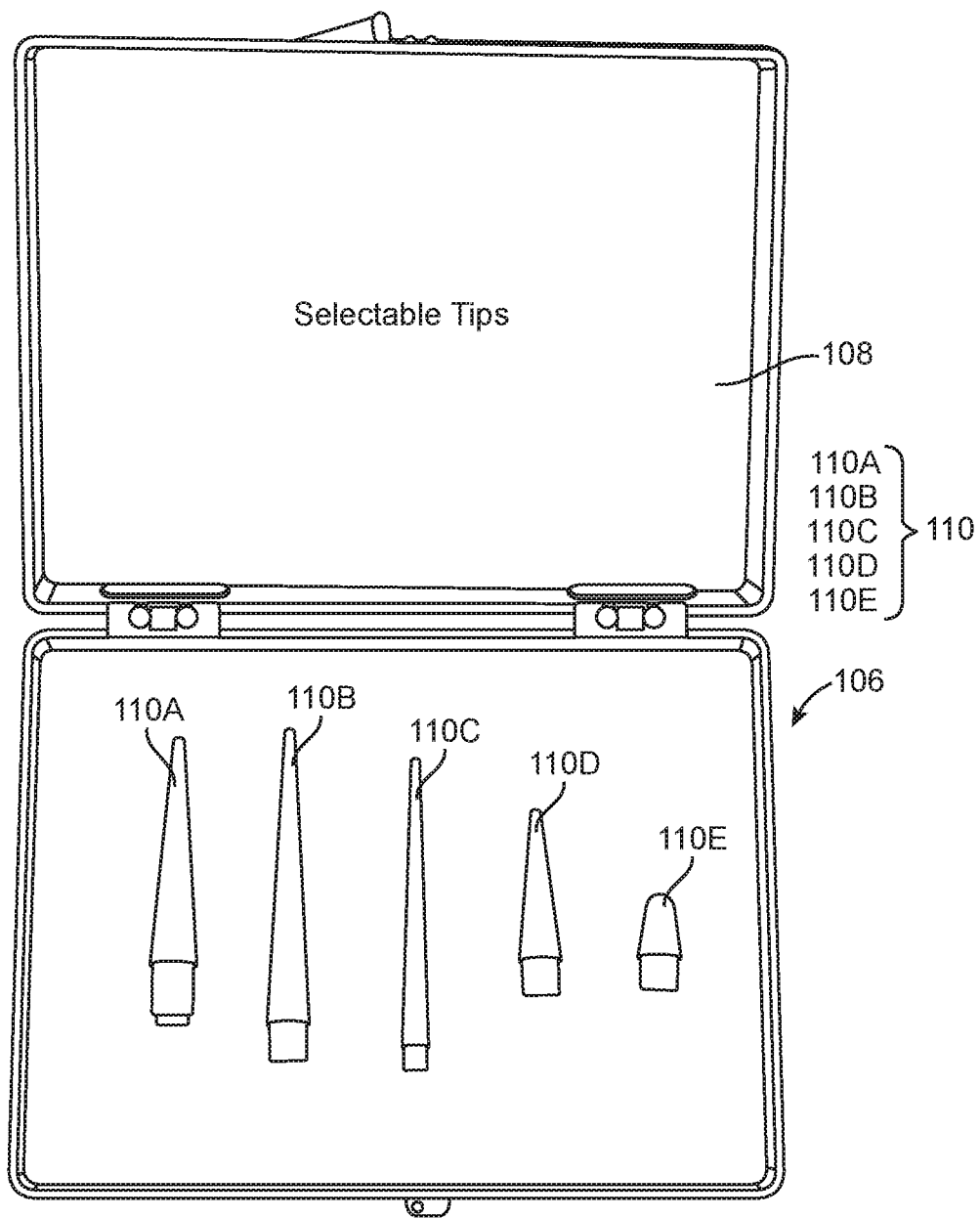
FIG. 2 is a perspective view of a selectable tip kit of the delivery system of FIG. 1 in accordance with one embodiment.

FIG. 2 is a perspective view of selectable tip kit 106 of delivery system 100 of FIG. 1 in accordance with one embodiment. Paying particular attention now to FIG. 2, selectable tip kit 106 is illustrated in an open state. For example, container 108 has been opened to expose the contents therein, including a plurality of different tips 110, sometimes called catheter tips or an array of catheter tips.

In accordance with this embodiment, there are five different tips 110A, 110B, 110C, 110D, 110E, collectively referred to as tips 110. Tips 110 have several different styles, shapes, and designs. Each tip 110 is uniquely shaped. As used herein, uniquely shaped means having a particular shape that is different than the shape of all the other tips 110. For example, tip 110A has a unique shape that is different than the unique shape of tips 110B, 110C, 110D, 110E. The same is true for each of tips 110B, 110C, 110D, 110E.

Each tip 110 is suitable for a particular procedure as determined by the physician. Prior to the procedure, the physician selects a desired tip 110, and attaches the selected tip 110 to catheter 104. Once attached to catheter 104, the tip 110 cannot be removed and the remaining unused tips 110 are discarded. Once the tip 110 is attached, catheter 104 is ready for tracking.

More particularly, delivery system 100 is packaged without a tip 110 attached to catheter 104. One tip 110 does not necessarily meet all applications. The physician chooses the particular tip 110 depending upon on the procedure the physician is encountering. Illustratively, the physician diagnoses the anatomy and the procedure to be performed and chooses the particular tip 110 that the physician concludes will be the best to work with and to make the procedure run smoothly.

Tips 110 are versatile and modular in style. The selected tip 110 is snapped onto the end of catheter 104 and the selected tip 110 is set. The tips 110 are a one-time use. Once the tip 110 is snapped into place, the tip 110 cannot be changed out again, e.g., without damage of catheter 104.

In one embodiment, tips 110 are very low cost and come in a plurality, e.g., four or five, with each delivery system 100. Unused tips 110 are discarded. Delivery system 100 is customizable to each procedure, putting the physician in control of the case. This provides a case specific delivery system for the physicians to use and at a very low expense and with minimal additional engineering.

Figure 3:
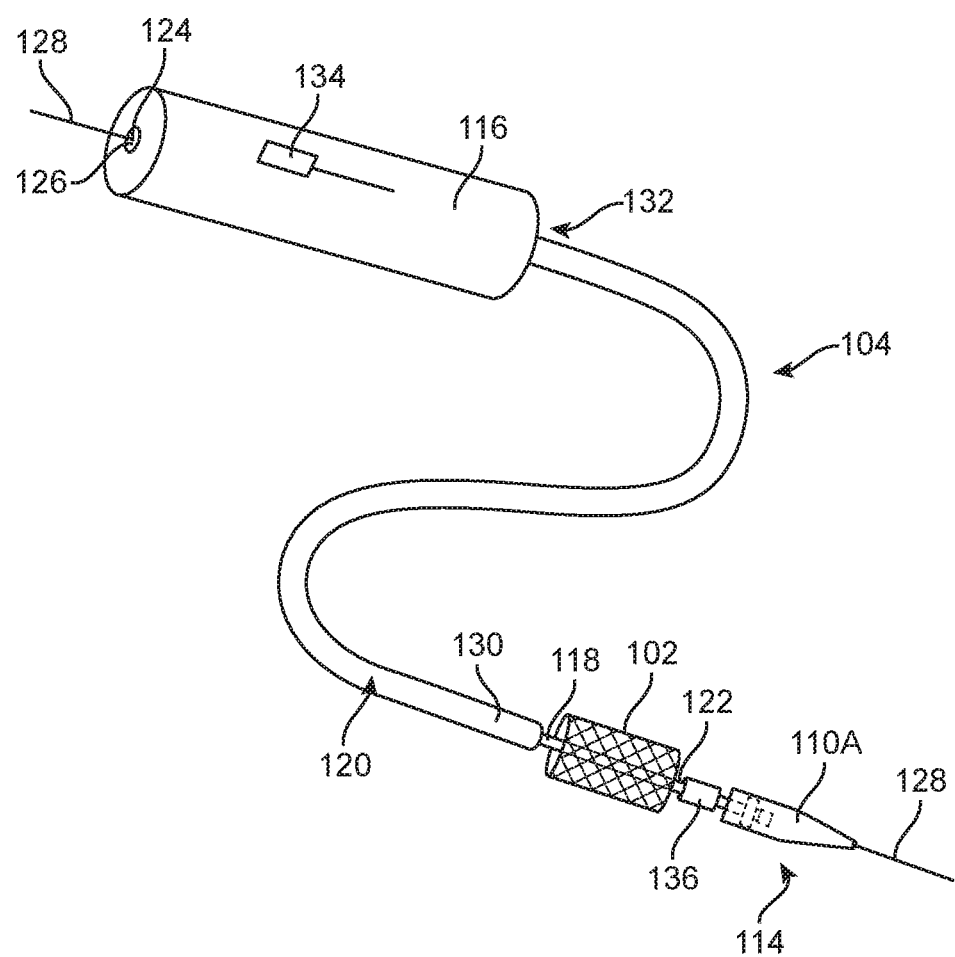
FIG. 3 is a perspective view of the delivery system after attachment of a tip to a catheter and during deployment of the prosthesis in accordance with one embodiment.

FIG. 3 is a perspective view of delivery system 100 after attachment of tip 110A to catheter 104 and during deployment of prosthesis 102 in accordance with one embodiment. For purposes of illustration, tip 110A has been selected as the desired tip of tips 110 by the physician as discussed above. However, in other procedures, the physician could have selected another of tips 110B, C, D, E. Accordingly, the discussion related to tip 110A is equally applicable to any one of tips 110.

Referring now to FIGS. 1-3, a tip attachment boss 112 is located at a distal end 114 of catheter 104. Tips 110 are configured to snap onto tip attachment boss 112. As discussed further below, tips 110 include a catheter interlock feature that is complimentary to tip attachment boss 112.

For purposes of clarity of discussion, as used herein, the distal end of catheter 104 is the end that is farthest from the operator (the end furthest from a handle 116) while the distal end of prosthesis 102 is the end nearest the operator (the end nearest handle 116), i.e., the distal end of catheter 104 and the proximal end of prosthesis 102 are the ends furthest from handle 116 while the proximal end of catheter 104 and the distal end of prosthesis 102 are the ends nearest handle 116. However, those of skill in the art will understand that depending upon the access location, the description of prosthesis 102 and catheter 104 may be consistent or opposite in actual usage.

Catheter 104 includes an inner member 118 and a sheath 120, sometimes called a catheter sheath. Inner member 118 includes a distal end 122 and a proximal end 124. Prosthesis 102 is placed over a portion of distal end 122 of inner member 118. In one embodiment, distal end 122 further includes radiopaque markers that allow the location of distal end 122 and prosthesis 102 to be determined. Proximal end 124 of inner member 118 terminates within and is mounted to handle 116 or extends through handle 116 and out a port 126 of handle 116.

In this embodiment, inner member 118 is a hollow tube whose interior acts as a guide wire lumen. A guide wire 128 extends through inner member 118 and extends out distal end 122. Guide wire 128 further extends through handle 116 and out port 126. Tip 110A tracks along guide wire 128.

Sheath 120 includes a distal end 130 and a proximal end 132. Prior to deployment, prosthesis 102 is radially compressed and restrained within distal end 130 of sheath 120. Proximal end 132 of sheath 120 extends into handle 116. Proximal end 132 of sheath 120 is coupled to a retraction mechanism 134 of handle 116. Sheath 120 is a hollow tube which acts as an inner member lumen. Inner member 118 extends through sheath 120.

During use, prosthesis 102 is placed over a portion of distal end 122 of inner member 118 and is radially compressed and restrained within distal end 130 of sheath 120 as illustrated in FIG. 1. Prosthesis 102 is introduced intravascularly and guided over guide wire 128 and by tip 110A to the treatment site, e.g., an aneurysm. Once prosthesis 102 is properly positioned, sheath 120 is retracted by handle 116 thus deploying prosthesis 102 as illustrated in FIG. 3. For example, prosthesis 102 is a radially expandable tubular prosthesis such as a stent, a stent-graft or other endovascular prosthesis and is used to treat one of several vascular conditions: abdominal aortic aneurysms, thoracic aortic aneurysm, thoracic aortic dissections, or other vascular conditions.

Figure 4:
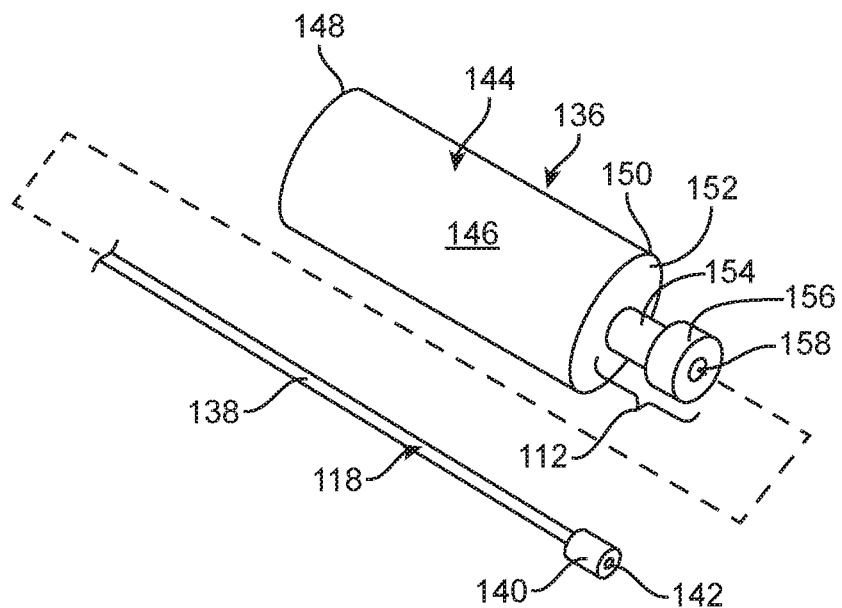
FIG. 4 is an exploded perspective view of an inner member and an attachment boss sleeve in accordance with one embodiment.
Figure 5:
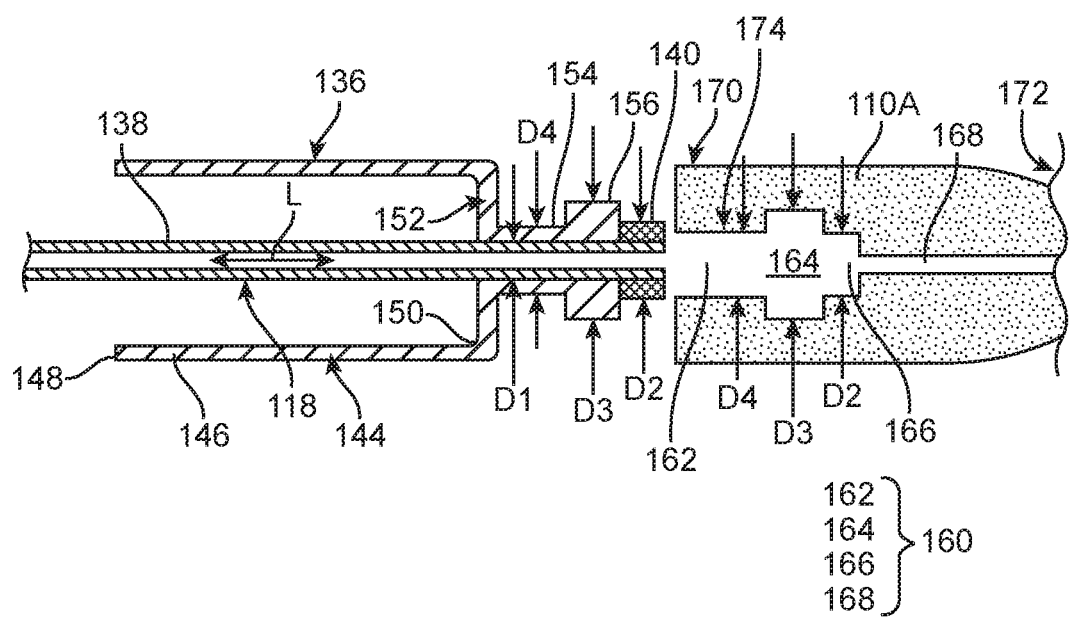
FIG. 5 is a cross-sectional view of the inner member, the attachment boss sleeve, and the tip in accordance with one embodiment.

FIG. 4 is an exploded perspective view of inner member 118 and an attachment boss sleeve 136 in accordance with one embodiment. FIG. 5 is a cross-sectional view of inner member 118, attachment boss sleeve 136, and tip 110A in accordance with one embodiment.

Referring now to FIGS. 4 and 5 together, inner member 118 includes a tube 138 and a stop 140. Tube 138, e.g., a Nitinol tube, sometimes called a Nitinol inner member, is a hollow cylindrical tube having a distal end 142. Stop 140, e.g., a hollow cylindrical tube, is mounted to distal end 142 of tube 138 to stop tube 138 from slipping out of attachment boss sleeve 136.

Attachment boss sleeve 136 includes a cylindrical hollow tubular body 144 and attachment boss 112. Tubular body 144 includes a hollow cylinder 146 having a proximal end 148 and a distal end 150. At distal end 150, tubular body 144 includes an end cap 152. End cap 152 is shaped as an annulus and lies in in a plane perpendicular to a longitudinal axis L of cylinder 146 and generally of catheter 104. End cap 152 extends radially inward from distal end 150 of cylinder 146.

Tip attachment boss 112 includes a hollow cylindrical shaft 154 and a flange 156. Shaft 154 extends from end cap 152 to flange 156. Flange 156 is annular (or ring-shaped).

A cylindrical inner member opening 158 extends through end cap 152, shaft 154, and flange 156. Tube 138 is configured to fit within inner member opening 158. Inner member opening 158 has a diameter D1 less than an outer diameter D2 of stop 140. Accordingly, stop 140 abuts against flange 156 and cannot pass through inner member opening 158. Inner member 118 supports attachment boss sleeve 136.

Flange 156 includes an outer diameter D3 greater than an outer diameter D4 of shaft 154. Diameter D2 of stop 140 is less than diameter D3 of flange 156 in accordance with this embodiment. In one embodiment, diameter D2 of stop 140 is equal to outer diameter D4 of shaft 154 but diameters D2, D4 are different in other embodiments. The difference between diameter D3 of flange 156 and diameter D4 of shaft 154 provides a tip snapping feature onto which tip 110A is snapped.

More particularly, tip 110A includes an internal variable diameter opening 160 which is configured to snap around attachment boss 112. In accordance with this embodiment, variable diameter opening 160 includes a shaft opening 162, a flange opening 164, a stop opening 166, and a guide wire opening 168. Shaft opening 162, flange opening 164, stop opening 166, and guide wire opening 168 collectively define variable diameter opening 160, i.e., are sections thereof.

Shaft opening 162 extends distally from a proximal end 170 of tip 110A to flange opening 164. Flange opening 164 extends distally from shaft opening 162 to stop opening 166. Stop opening 166 extends distally from flange opening 164 to guide wire opening 168. Guide wire opening 168 extends distally from stop opening 166 completely through tip 110A to a distal end 172 of tip 110A. Generally, internal variable diameter opening 160 including shaft opening 162, flange opening 164, stop opening 166, and guide wire opening 168 extend longitudinally and centrally through tip 110A from proximal end 170 to distal end 172 of tip 110A.

Shaft opening 162, flange opening 164, and stop opening 166 are configured to fit around shaft 154, flange 156, and stop 140, respectively. Shaft opening 162, flange opening 164, and stop opening 166 have the same diameters D4, D3, D2 as shaft 154, flange 156, and stop 140, respectively. Although it is described that the diameters of the features are equal, it is to be understood that the diameters may not be exactly equal, but are approximately equal such that shaft opening 162, flange opening 164, and stop opening 166 can fit around shaft 154, flange 156, and stop 140, respectively, as described further below in reference to FIG. 6. Guide wire opening 168 is configured to fit around guide wire 128.

Figure 6:
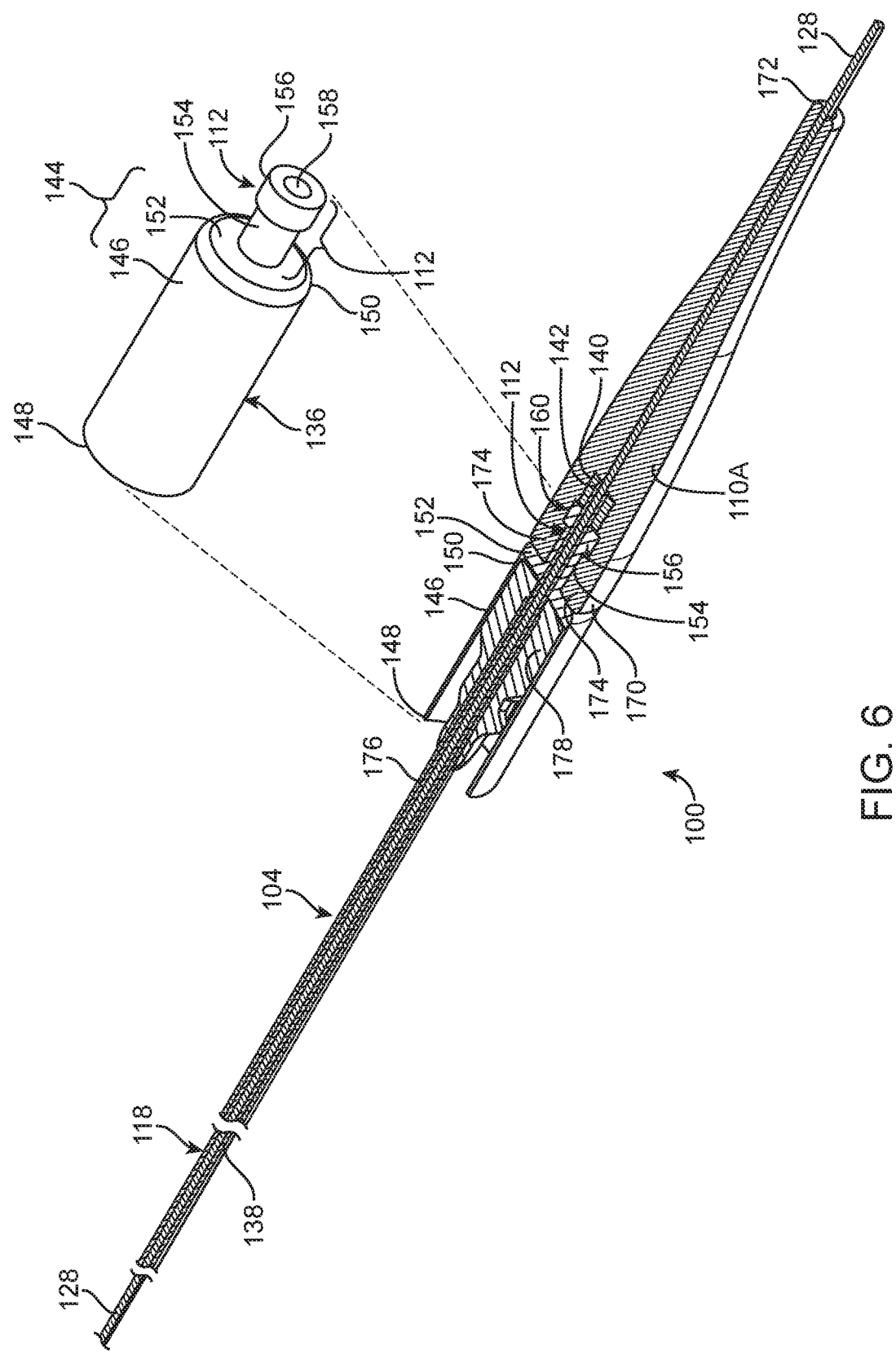
FIG. 6 is a cross-sectional view of the delivery system having the tip attached to the catheter in accordance with one embodiment.

FIG. 6 is a cross-sectional view of delivery system 100 having tip 110A attached to catheter 104 in accordance with one embodiment. Referring now to FIGS. 3-6, shaft opening 162, flange opening 164, and stop opening 166 of tip 110A are snapped around shaft 154, flange 156, and stop 140, respectively. Guide wire 128 passes through tube 138 of inner member 118, exits inner member 118, and passes through and out of guide wire opening 168 of tip 110A.

The portion of tip 110A at (around) shaft opening 162 is referred to as a snap 174. The inner diameter of snap 174 is diameter D4 which is less than diameter D3 of flange 156. Accordingly, snap 174 must be stretched around flange 156 and then snaps around shaft 154. Tip 110A is made of a flexible resilient material such that snap 174 can stretch around flange 156. For example, tip 110A is a thermoplastic elastomer made of flexible polyether and rigid polyamide, e.g., is PEBAX® 4033, although other flexible resilient materials are used in other embodiments. Once snap 174 snaps into place, tip 110A is permanently mounted to catheter 104. Generally, snap 174 is configured to snap onto tip attachment boss 112.

In accordance with this embodiment, referring to FIGS. 3 and 6 together, catheter 104 includes a spindle tube 176 and a spindle 178. Spindle 178 in cooperation with cylinder 146 of attachment boss sleeve 136 is configured to hold the proximal end of prosthesis 102 in place while sheath 120 is withdrawn. Spindle 178 is then moved out of attachment boss sleeve 136 to release the proximal end of prosthesis 102. For example, spindle tube 176 extends into handle 116 and handle 116 includes a mechanism to retract spindle tube 176 and thus spindle 178. Although spindle tube 176 and spindle 178 are illustrated and described, in another embodiment, catheter 104 is formed without spindle tube 176 and spindle 178.

Figure 7:
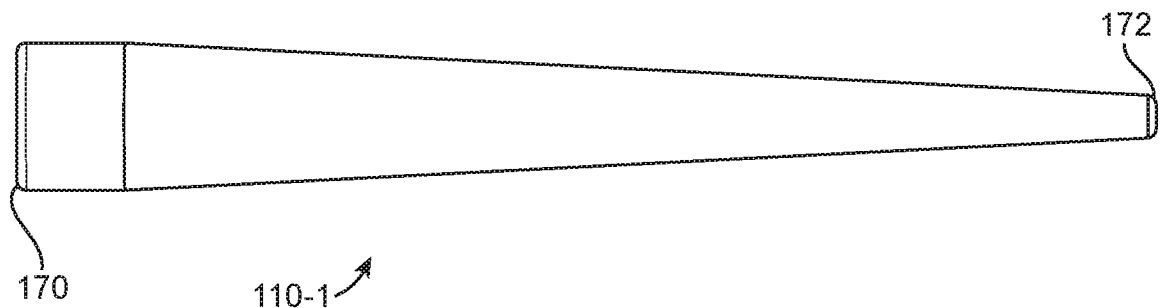
FIG. 7 is a side plan view of an attachable tip in accordance with one embodiment.
Figure 8:
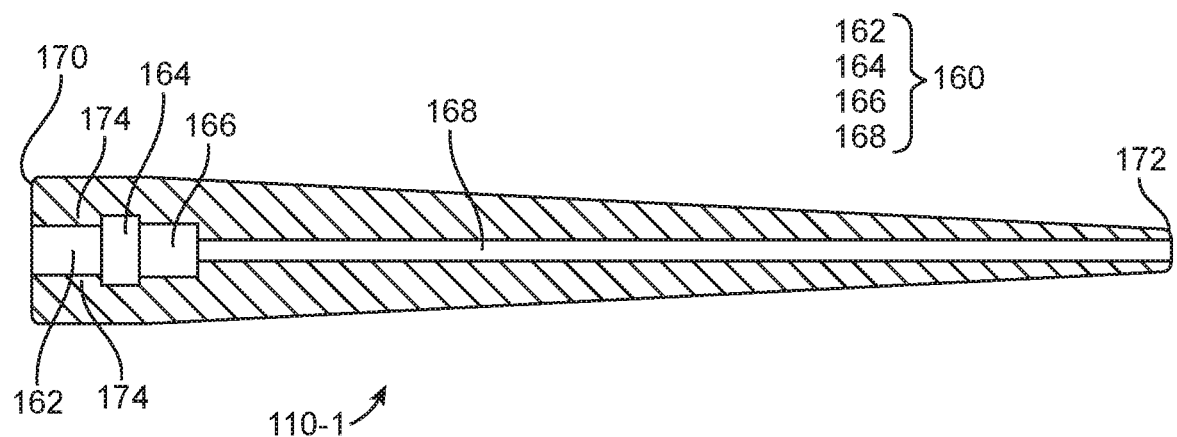
FIG. 8 is a cross-sectional view of the tip of FIG. 7.

FIG. 7 is a side plan view of an attachable tip 110-1 in accordance with one embodiment. FIG. 8 is a cross-sectional view of tip 110-1 of FIG. 7. Referring now to FIGS. 7 and 8 together, tip 110-1 has a relatively uniform taper extending to distal end 172. The length and width (diameter) of tip 110-1 is sometimes referred to as a standard length and width for comparison to the lengths of tips described below. Tip 110-1 is for general use but can be used in a wide variety of procedures.

Figure 9:
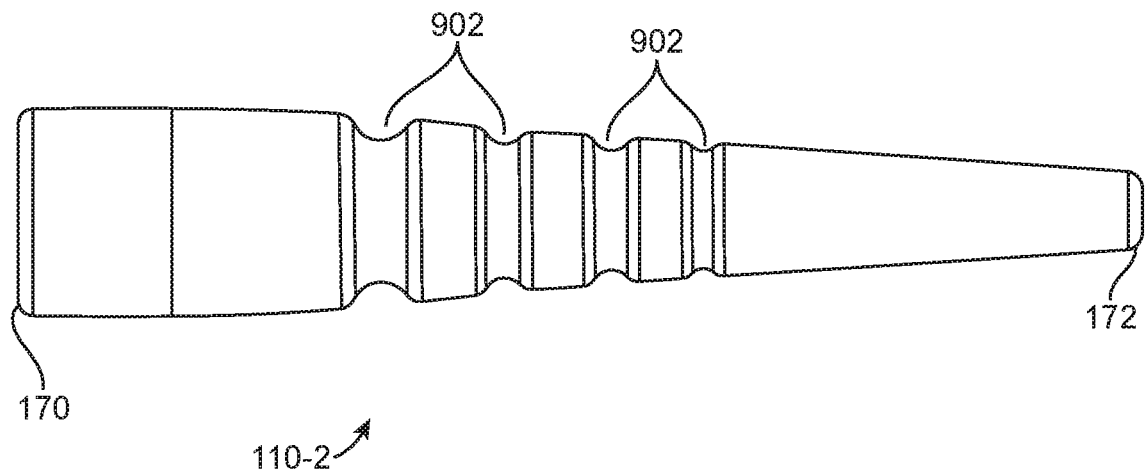
FIG. 9 is a side plan view of an attachable tip in accordance with another embodiment.
Figure 10:
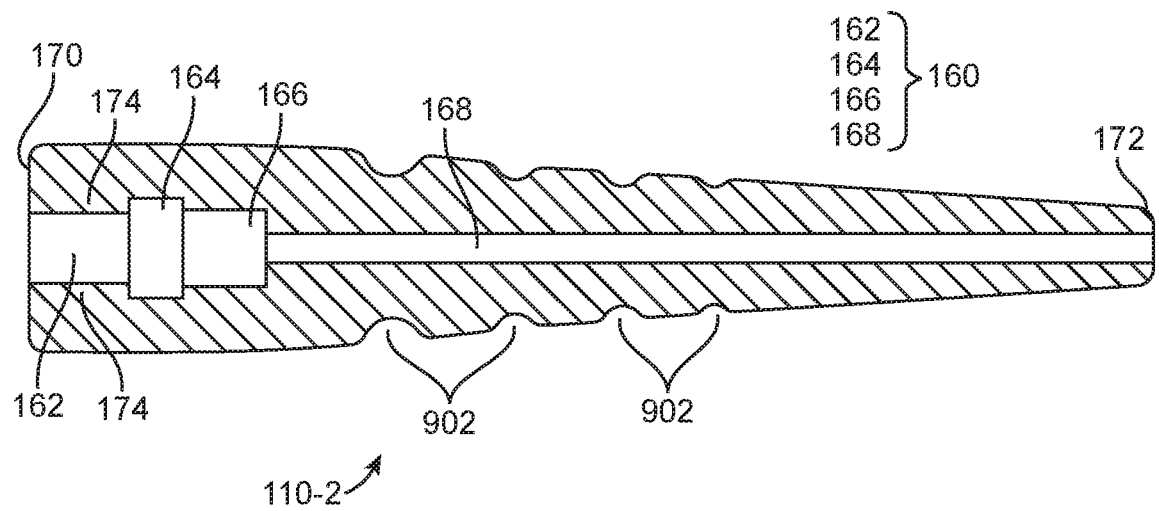
FIG. 10 is a cross-sectional view of the tip of FIG. 9.

FIG. 9 is a side plan view of an attachable tip 110-2 in accordance with one embodiment. FIG. 10 is a cross-sectional view of tip 110-2 of FIG. 9. Referring now to FIGS. 9 and 10 together, tip 110-2 has a plurality of circumferential grooves 902. Grooves 902 are reduced thickness areas that have increased flexibility as compared to the areas of tip 110-2 where grooves 902 are not formed.

In one embodiment, tip 110-2 of FIGS. 9-10 is shorter than tip 110-1 of FIGS. 7-8. Tip 110-2 is sometimes called a medium length tip with flexible grooves. In one example, tip 110-2 is suitable for use in the thoracic region, e.g., to access the left subclavian artery. However, tip 110-2 can be used in a wide variety of procedures.

Figure 11:
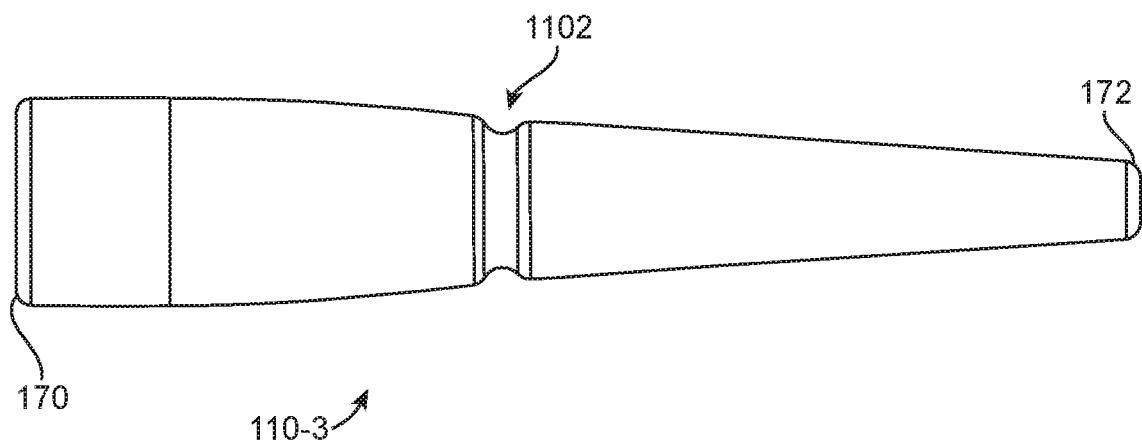
FIG. 11 is a side plan view of an attachable tip in accordance with another embodiment.
Figure 12:
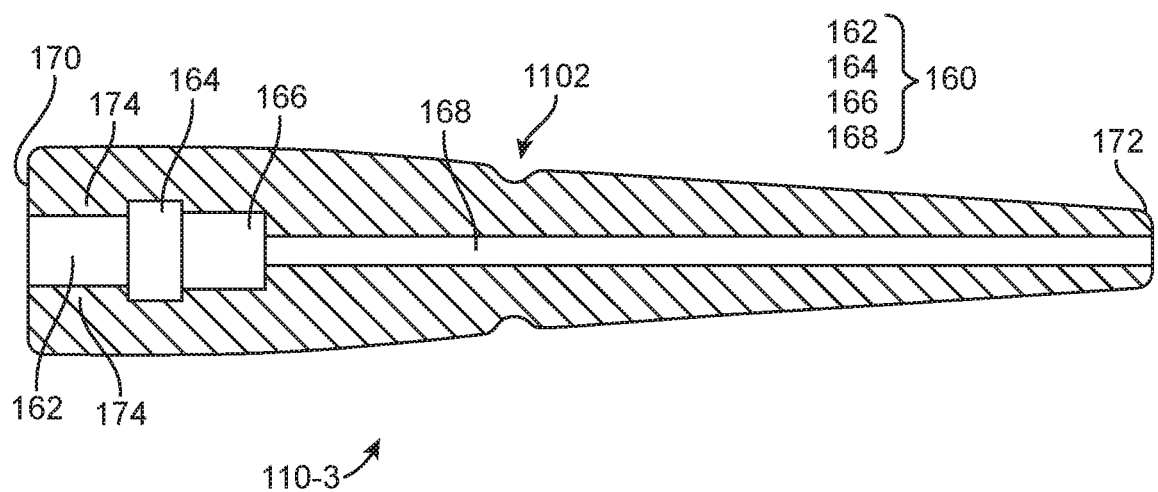
FIG. 12 is a cross-sectional view of the tip of FIG. 11.

FIG. 11 is a side plan view of an attachable tip 110-3 in accordance with one embodiment. FIG. 12 is a cross-sectional view of tip 110-3 of FIG. 11. Referring now to FIGS. 11 and 12 together, tip 110-3 has a single circumferential groove 1102. Groove 1102 is a reduced thickness area that has increased flexibility as compared to the areas of tip 110-3 where groove 1102 is not formed.

In one embodiment, tip 110-3 of FIGS. 11-12 is shorter than tip 110-1 of FIGS. 7-8. Tip 110-3 is sometimes called a medium length tip with a flexible groove and can be used in a wide variety of different procedures.

Figure 13:
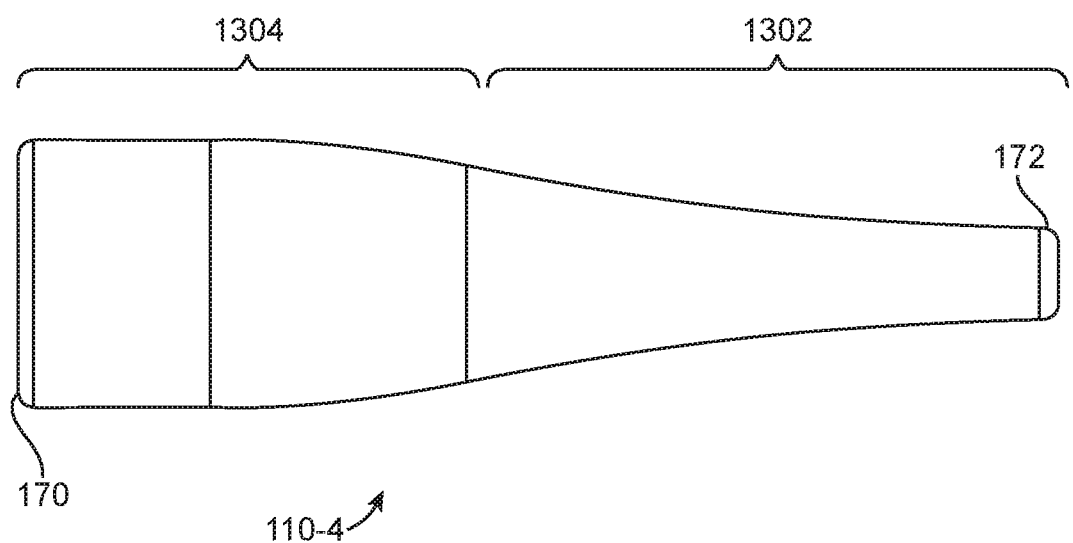
FIG. 13 is a side plan view of an attachable tip in accordance with another embodiment.
Figure 14:
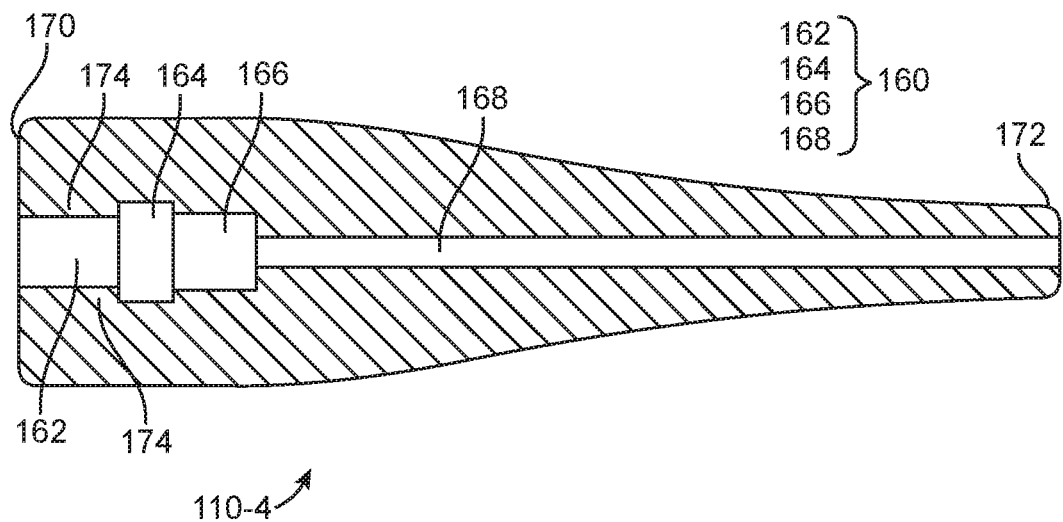
FIG. 14 is a cross-sectional view of the tip of FIG. 13.

FIG. 13 is a side plan view of an attachable tip 110-4 in accordance with one embodiment. FIG. 14 is a cross-sectional view of tip 110-4 of FIG. 13. Referring now to FIGS. 13 and 14 together, tip 110-4 has a flexible distal section 1302 and a rigid proximal section 1304. Tip 110-4 is sometimes called a short taper tip and is suitable for general use and can be used in wide variety of different procedures.

Figure 15:
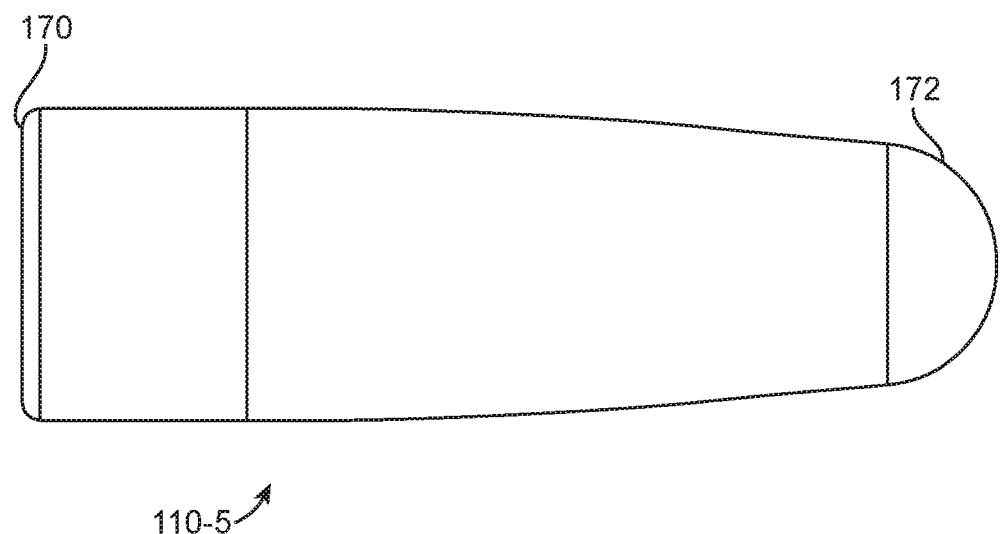
FIG. 15 is a side plan view of an attachable tip in accordance with another embodiment.
Figure 16:
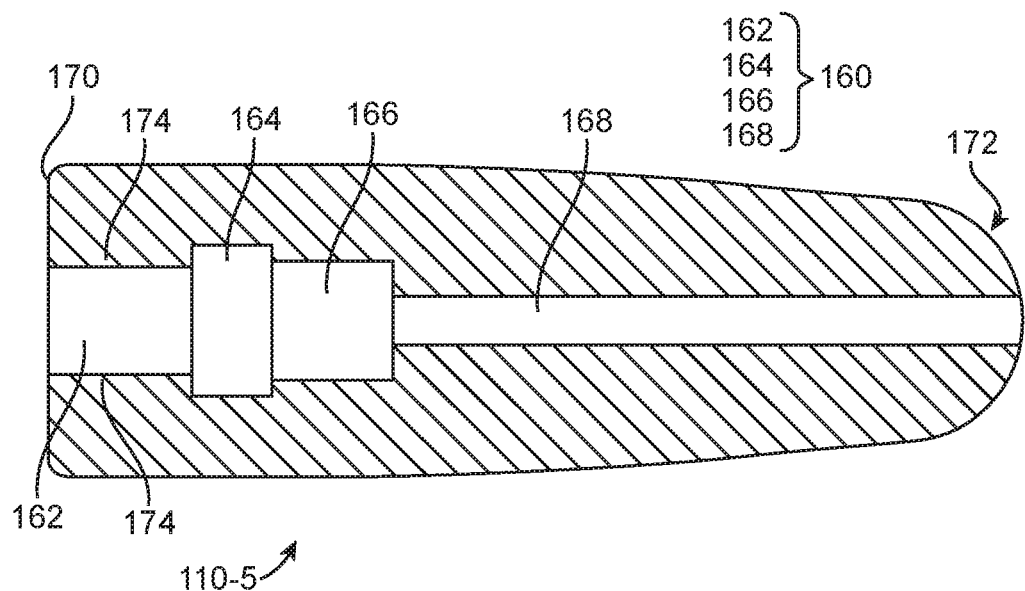
FIG. 16 is a cross-sectional view of the tip of FIG. 15.

FIG. 15 is a side plan view of an attachable tip 110-5 in accordance with one embodiment. FIG. 16 is a cross-sectional view of tip 110-5 of FIG. 15. Referring now to FIGS. 15 and 16 together, tip 110-5 is short and bullet shaped. More particularly, tip 110-5 of FIGS. 15-16 is shorter than tip 110-1 of FIGS. 7-8

Tip 110-5 is suitable for procedures close to the heart. However, tip 110-5 can be used in a wide variety of different procedures.

Figure 17:
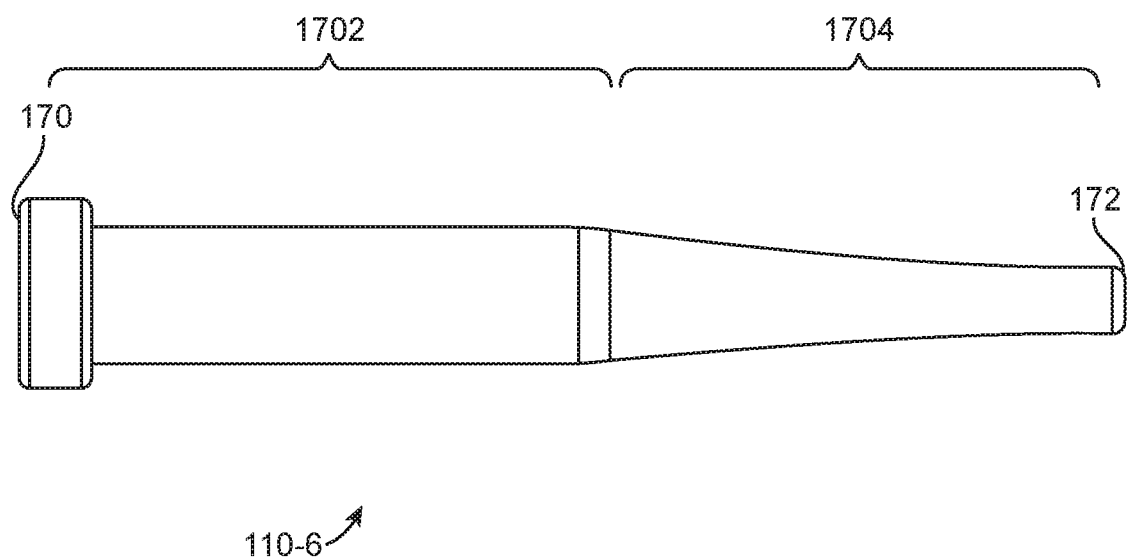
FIG. 17 is a side plan view of an attachable tip in accordance with another embodiment.
Figure 18:
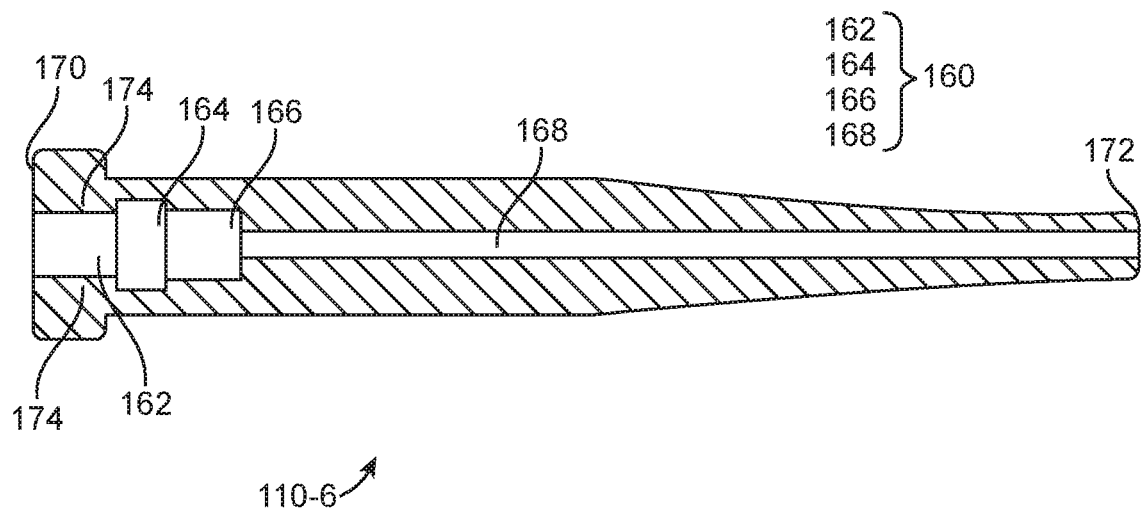
FIG. 18 is a cross-sectional view of the tip of FIG. 17.

FIG. 17 is a side plan view of an attachable tip 110-6 in accordance with one embodiment. FIG. 18 is a cross-sectional view of tip 110-6 of FIG. 17. Referring now to FIGS. 17 and 18 together, tip 110-6 is narrower as compared to tip 110-1 of FIGS. 7-8. Due to being narrow, tip 110-6 is relatively flexible. Tip 110-6 has a uniform diameter proximal section 1702 and a tapering distal section 1704. Distal section 1704 is more flexible than proximal section 1702.

Tip 110-6 is particular well suited to access narrow vessels but can be used in wide variety of procedures.

Figure 19:
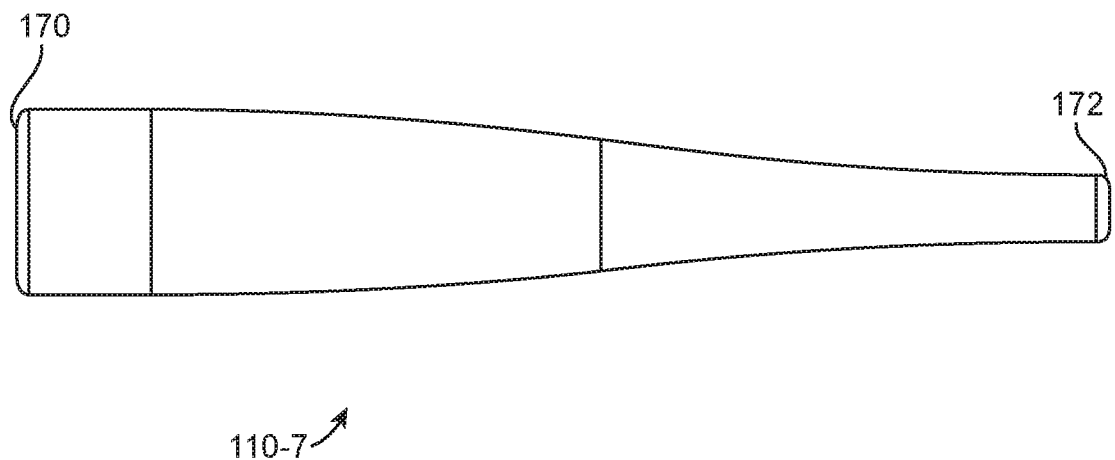
FIG. 19 is a side plan view of an attachable tip in accordance with another embodiment.
Figure 20:
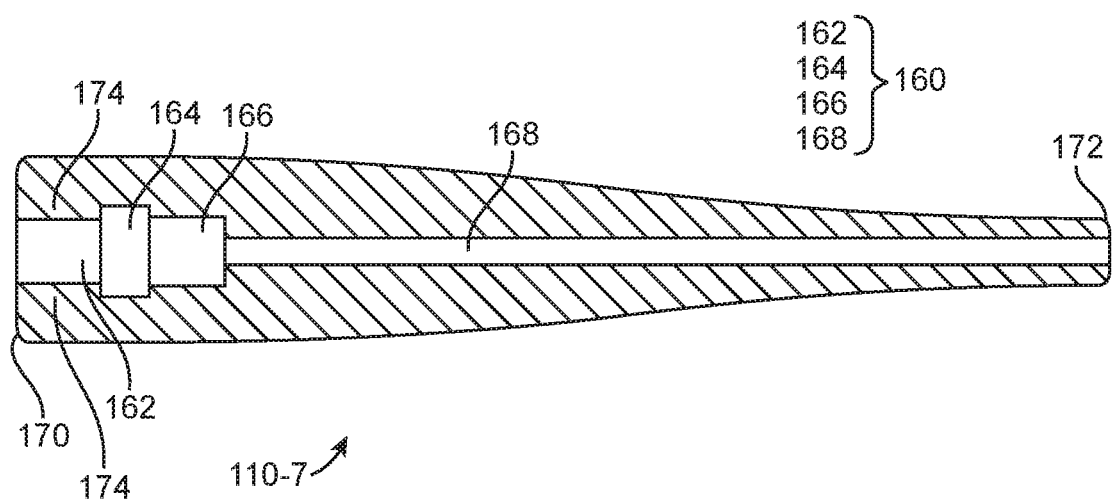
FIG. 20 is a cross-sectional view of the tip of FIG. 19.

FIG. 19 is a side plan view of an attachable tip 110-7 in accordance with one embodiment. FIG. 20 is a cross-sectional view of tip 110-7 of FIG. 19. Referring now to FIGS. 19 and 20 together, tip 110-7 is narrower as compared to tip 110-1 of FIGS. 7-8. Due to being narrow, tip 110-7 is relatively flexible. Tip 110-7 tapers to the distal end 172.

Tip 110-7 is particular well suited to access narrow vessels but can be used in wide variety of procedures.

Paying particular attention now to FIGS. 8, 10, 12, 14, 16, 18, 20, tips 110-1, 110-2, 110-3, 110-4, 110-5, 110-6, 110-7 (collectively referred to as tips 110) are all representative of one of tips 110 of selectable tip kit 106 of FIG. 2 in one embodiment. Although tips 110 have unique shapes and are better suited for some procedures than others, internally, tips 110 have an identical configuration (are modular) to allow tips 110 to be attached to catheter 104 as described above. Specifically, tips 110 have identical shaft openings 162, flange openings 164, stop openings 166, and snaps 174. Guide wire openings 168 are generally of the same diameter however, are longer or shorter depending upon the particular tip.

Although particular tips are described above, other attachable tips are used in other embodiments depending upon the particular procedure being performed and as desired, e.g., by the physician.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A delivery system comprising:
    a catheter comprising:
        a tip attachment boss comprising:
            a shaft;
            a flange; and
            a cylindrical inner member opening extending through the shaft and the flange; and
        an inner member comprising a tube within the cylindrical inner member opening;
    a selectable tip kit comprising a plurality of uniquely shaped tips, each tip includes a snap, each tip being configured to non-removably snap onto the tip attachment boss and including a guide wire opening extending through the tip, wherein the snap is configured to stretch around the flange and non-removably snap around the shaft; and
    a guidewire configured to extend through the guide wire opening.

2. The delivery system of claim 1 wherein the selectable tip kit comprises a container containing the tips.

3. The delivery system of claim 1 wherein the tips comprise a first tip and a second tip, the first tip being longer than the second tip.

4. The delivery system of claim 1 wherein the tips comprise a first tip and a second tip, the first tip being thinner than the second tip.

5. The delivery system of claim 1 wherein the snap is configured to non-removably snap onto the tip attachment boss to mount the tip to the catheter.

6. The delivery system of claim 1 wherein the snap in each tip is identical.

7. The delivery system of claim 1 wherein the catheter comprises:
    a sheath; and
    a prosthesis within the sheath.

8. The delivery system of claim 1 wherein the tip attachment boss is at a distal end of the catheter.

9. The delivery system of claim 1 wherein the catheter further comprises:
    an attachment boss sleeve including a cylindrical hollow tubular body and the tip attachment boss;
    a spindle; and
    a prosthesis comprising a proximal end held between a hollow cylinder of the cylindrical hollow tubular body and the spindle.

10. The delivery system of claim 9 wherein the cylindrical hollow tubular body further comprises an end cap at a distal end of the hollow cylinder, the shaft extending from the end cap to the flange.

11. A method comprising:
    supporting a tip attachment boss on an inner member, the inner member comprising a tube and a stop;
    providing a delivery system comprising a catheter and a selectable tip kit comprising a plurality of uniquely shaped tips, each of the tips including a guide wire opening extending through the tip, wherein the catheter comprises the inner member and the tip attachment boss, the tip attachment boss comprising a shaft and a flange, the tube extending through the shaft and the flange and the stop abutting the flange;
    selecting one tip of the tips; and
    non-removably attaching the one tip to the catheter comprising stretching a snap of the tip around the flange and non-removably snapping the snap around the shaft.

12. The method of claim 11 wherein the non-removably attaching the one tip comprises snapping the one tip to an attachment boss sleeve of the catheter.

13. The method of claim 12 further comprising:
    restraining a prosthesis within a sheath of the catheter;
    holding a proximal end of the prosthesis between a hollow cylinder of a cylindrical hollow tubular body of the attachment boss sleeve and a spindle;
    retracting the sheath; and
    moving the spindle out of the hollow cylinder to release the proximal end of the prosthesis.

14. The method of claim 11 wherein the tips are a one-time use.

15. The method of claim 14 further comprising discarding all the tips except the one tip attached to the catheter.

16. The method of claim 11 further comprising tracking the tip along a guidewire extending through the guidewire opening.

17. The method of claim 11 wherein the non-removably attaching further comprises snapping a stop opening of the one tip around the stop.

18. A delivery system comprising:
    a catheter comprising:
        a tip attachment boss comprising:
            a shaft;
            a flange; and
            a cylindrical inner member opening extending through the shaft and the flange; and
        an inner member comprising a tube within the cylindrical inner member opening, the inner member further comprises a stop coupled to a distal end of the tube; and
    a selectable tip kit comprising a plurality of uniquely shaped tips, each tip includes a snap, each tip being configured to non-removably snap onto the tip attachment boss and including a guide wire opening extending through the tip, wherein the snap is configured to stretch around the flange and non-removably snap around the shaft, wherein each tip includes a stop opening configured to fit around the stop.

* * * * *